United States Patent
Ohishi (10) Patent No.: US 11,246,492 B2
(45) Date of Patent: Feb. 15, 2022

(54) APPARATUS PERFORMING EXAMINATION UTILIZING PHOTOACOUSTIC EFFECT, EXAMINATION SUPPORT METHOD, AND PROGRAM

(71) Applicant: CANON KABUSHIKI KAISHA, Tokyo (JP)

(72) Inventor: Shinji Ohishi, Oyama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1016 days.

(21) Appl. No.: 15/754,999

(22) PCT Filed: Aug. 24, 2016

(86) PCT No.: PCT/JP2016/003852
§ 371 (c)(1),
(2) Date: Feb. 23, 2018

(87) PCT Pub. No.: WO2017/038054
PCT Pub. Date: Mar. 9, 2017

(65) Prior Publication Data
US 2020/0229705 A1    Jul. 23, 2020

(30) Foreign Application Priority Data

Aug. 31, 2015    (JP) .............................. JP2015-170600

(51) Int. Cl.
*A61B 5/00*    (2006.01)
*G16H 50/20*    (2018.01)
(Continued)

(52) U.S. Cl.
CPC ............ *A61B 5/0095* (2013.01); *A61B 5/742* (2013.01); *G16H 30/40* (2018.01); *G16H 40/63* (2018.01);
(Continued)

(58) Field of Classification Search
CPC combination set(s) only.
See application file for complete search history.

(56) References Cited

U.S. PATENT DOCUMENTS

2007/0232907 A1    10/2007    Pelissier
2008/0031503 A1*   2/2008    Kanada .................. G16H 15/00
                                                  382/128
(Continued)

FOREIGN PATENT DOCUMENTS

CN    104605816 A    5/2015
EP      2868262 A1    5/2015
(Continued)

OTHER PUBLICATIONS

Minghua Xu et. al., Universal Back-Projection Algorithm for Photoacoustic Computed Tomography, Physical Review E 71, 016706 (2005).

*Primary Examiner* — Joel F Brutus
(74) *Attorney, Agent, or Firm* — Canon U.S.A., Inc. IP Division (57) ABSTRACT

The present invention provides an apparatus which efficiently perform an examination based on an examination order. The apparatus includes a connection unit configured to be connected to a plurality of measurement units each of which includes a light irradiation unit which irradiates a subject with light and a reception unit which receives an acoustic wave generated from the subject irradiated with the light, a first obtaining unit configured to obtain information on an examination order; a second obtaining unit configured to obtain information on a selected one of the measurement units connected to the connection unit, and a determination unit configured to determine whether the selected measurement unit is suitable for the examination order in accordance (Continued)

with the information on the examination order and the information on the selected measurement unit.

15 Claims, 7 Drawing Sheets

(51) Int. Cl.
*G16H 30/40* (2018.01)
*G16H 40/63* (2018.01)
*G16H 30/20* (2018.01)

(52) U.S. Cl.
CPC ............ *G16H 50/20* (2018.01); *A61B 5/7495* (2013.01); *A61B 2560/0266* (2013.01); *G16H 30/20* (2018.01)

(56) References Cited

U.S. PATENT DOCUMENTS

| | | | |
|---|---|---|---|
| 2014/0051970 A1 | 2/2014 | Ebisawa | |
| 2014/0180087 A1* | 6/2014 | Millett | A61B 8/12 600/437 |

FOREIGN PATENT DOCUMENTS

| | | |
|---|---|---|
| JP | 2003-323494 A | 11/2003 |
| JP | 2010-253031 A | 11/2010 |
| JP | 2011-72526 A | 4/2011 |
| JP | 2013-121490 A | 6/2013 |
| JP | 2013-121491 A | 6/2013 |
| JP | 2014-100456 A | 6/2014 |
| JP | 2015-84937 A | 5/2015 |
| JP | 2015-154916 A | 8/2015 |

\* cited by examiner

| EXAMINEE ID | EXAMINATION ID | EXAMINATION PORTION | EXAMINATION TARGET | EXAMINATION DEPTH |
|---|---|---|---|---|
| A | A01 | RIGHT BREAST | OXYGEN SATURATION IN BLOOD VESSEL | 40 mm |
| A | A02 | LEFT BREAST | OXYGEN SATURATION IN BLOOD VESSEL | 40 mm |
| B | B01 | HAND | FORM OF BLOOD VESSEL | 5 mm |
| C | C01 | FACE | AMOUNT OF SKIN COLLAGEN | 0.5 mm |
| ... | ... | ... | ... | ... |

[Fig. 6A]

|  | HARDWARE ID (EXAMINATION APPARATUS INFORMATION) | | |
|---|---|---|---|
| EXAMINATION PORTION | LIGHT SOURCE ID | PROBE ID | DAS ID |
| BREAST | any | 10, 11, 12 | any |
| FACE | any | 13, 14 | any |
| HAND | any | 15, 16 | any |
| LEG | any | 17, 18 | any |
| ... | ... | ... | ... |

[Fig. 6B]

|  | HARDWARE ID (EXAMINATION APPARATUS INFORMATION) | | |
|---|---|---|---|
| EXAMINATION TARGET | LIGHT SOURCE ID | PROBE ID | DAS ID |
| FORM OF BLOOD VESSEL | 20, 21, 22 | 10, 13, 15 | 30, 31, 32 |
| OXYGEN SATURATION IN BLOOD VESSEL | 22, 23, 24, 25 | 11, 14, 16, 18 | 30, 31 |
| AMOUNT OF SKIN COLLAGEN | 22, 24, 25, 26 | 11, 14, 16, 18 | 33 |
| ... | ... | ... | ... |

[Fig. 7]

| EXAMINATION TARGET | APPARATUS PARAMETER | | | |
|---|---|---|---|---|
| | LIGHT WAVELENGTH | RECEPTION BAND (CENTER FREQUENCY) | SAMPLING FREQUENCY | ... |
| FORM OF BLOOD VESSEL | 514, 797, OR 1100 [nm] | 5 [MHz] | 40 [MHz] | ... |
| OXYGEN SATURATION IN BLOOD VESSEL | 756 AND 797 [nm] | 5 [MHz] | 40 [MHz] | ... |
| AMOUNT OF SKIN COLLAGEN | 700 AND 750 [nm] | 1 [MHz] | 8 [MHz] | ... |
| ... | ... | ... | ... | ... |

[Fig. 8]

| APPARATUS PARAMETER | | | |
|---|---|---|---|
| LIGHT WAVELENGTH | RECEPTION BAND | SAMPLING FREQUENCY | ... |
| 1100 [nm] | 5 [MHz] | 40 [MHz] | ... |

APPARATUS PERFORMING EXAMINATION UTILIZING PHOTOACOUSTIC EFFECT, EXAMINATION SUPPORT METHOD, AND PROGRAM

TECHNICAL FIELD

The present invention relates to an apparatus utilizing a photoacoustic effect.

BACKGROUND ART

Photoacoustic apparatuses which obtain information on a subject (subject information) based on acoustic waves (photoacoustic waves) generated by irradiating the subject with light have been actively studied mainly in a medical field. PTL1 discloses a photoacoustic apparatus which obtains oxygen saturation and fat concentration to be used in diagnosis.

CITATION LIST

Patent Literature

PTL 1: Japanese Patent Laid-Open No. 2014-100456

SUMMARY OF THE INVENTION

As a procedure of a diagnosis performed by a photoacoustic apparatus, a doctor may offer an examination order for specifying an examination portion to a laboratory technician. The examination order may be offered as a printing matter (including a medical record written by hand) or electronic information (an electronic medical record) through a network. Then an examinee may be examined after the laboratory technician checks whether a connection of hardware suitable for the examination order and a setting of apparatus parameters have been performed.

However, in the diagnosis using the photoacoustic apparatus, a procedure of the examination based on the examination order is complicated, and the complicated procedure is to be coped with to effectively perform the examination.

Accordingly, the present invention provides an apparatus capable of efficiently performing an examination based on an examination order.

The present invention provides an apparatus including a connection unit configured to be connected to a plurality of measurement units each of which includes a light irradiation unit which irradiates a subject with light and a reception unit which receives an acoustic wave generated from the subject irradiated with the light, a first obtaining unit configured to obtain information on an examination order, a second obtaining unit configured to obtain information on a selected one of the measurement units connected to the connection unit, and a determination unit configured to determine whether the selected measurement unit is suitable for the examination order in accordance with the information on the examination order and the information on the selected measurement unit.

Further features of the present invention will become apparent from the following description of exemplary embodiments with reference to the attached drawings.

DESCRIPTION OF EMBODIMENT

Figure 1:
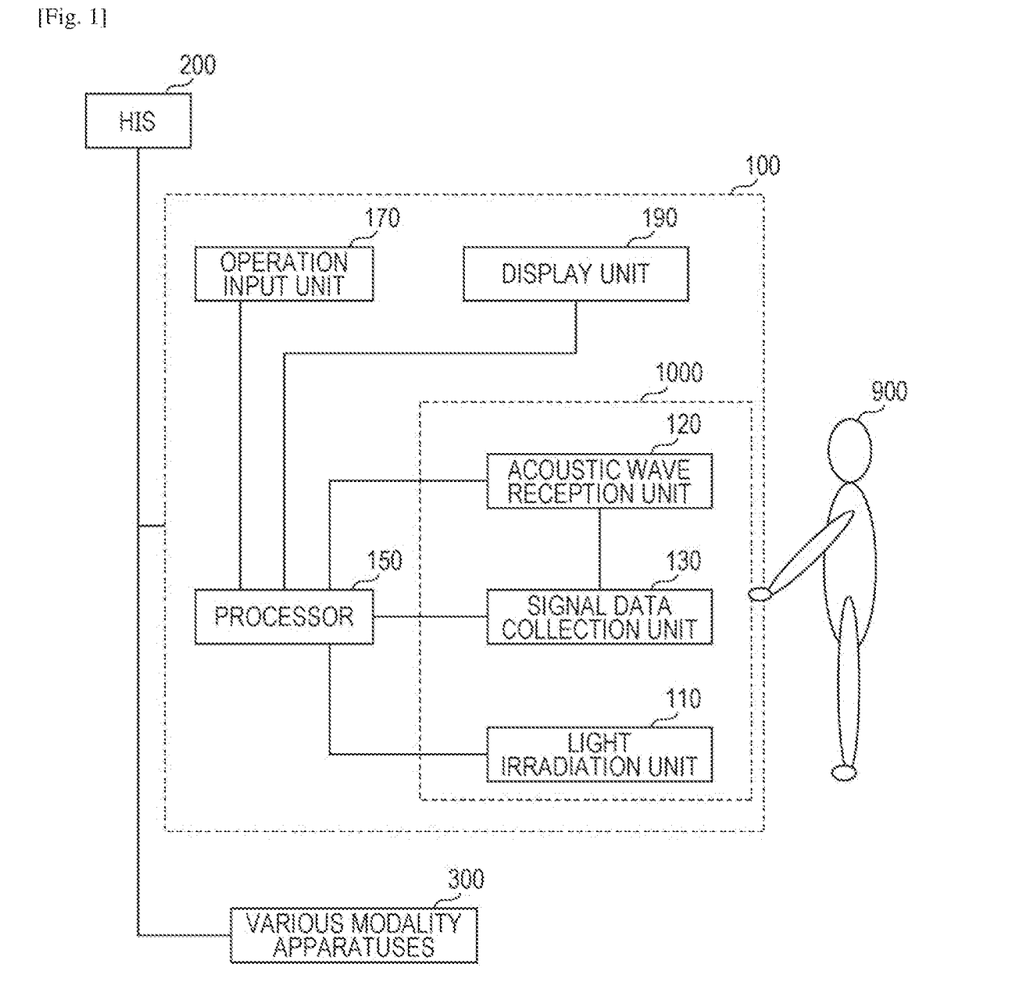
FIG. 1 is a block diagram illustrating an examination system according to an embodiment.

The present invention is applied to an examination system including a photoacoustic apparatus 100 as illustrated in FIG. 1. FIG. 1 is a block diagram illustrating the examination system according to an embodiment.

The examination system of this embodiment includes the photoacoustic apparatus 100, a hospital information system (HIS) 200, and various modality apparatuses 300. The photoacoustic apparatus 100 and the various modality apparatuses 300 receive an examination order from the HIS 200 and perform an examination in accordance with the examination order. Examples of the HIS 200 which transmits the examination order include a radiology information system (RIS). The various modality apparatuses 300 mean modality apparatuses other than the photoacoustic apparatus 100. Examples of the various modality apparatuses 300 include a computer tomography (CT) apparatus and a magnetic resonance imaging (MRI) apparatus.

The photoacoustic apparatus 100 includes a light irradiation unit 110, an acoustic wave reception unit 120, a signal data collection unit 130, a processor 150, an operation input unit 170, and a display unit 190. The light irradiation unit 110, the acoustic wave reception unit 120, and the signal data collection unit 130 are included in a photoacoustic measurement unit 1000.

When the light irradiation unit 110 irradiates a subject 900 with light, acoustic waves are generated in the subject 900. Acoustic waves generated due to a photoacoustic effect in response to light is referred to as "photoacoustic waves". The acoustic wave reception unit 120 receives a photoacoustic wave and outputs an analog electric signal. The signal data collection unit 130 converts the analog electric signal output from the acoustic wave reception unit 120 into a digital electric signal to be output to the processor 150. The processor 150 stores the digital signal supplied from the signal data collection unit 130 as signal data derived from the photoacoustic wave. Note that a process from the irradiation with light to the output of the digital signal to be stored as signal data is referred to as "photoacoustic measurement". The hardware units used in the photoacoustic measurement constitute the photoacoustic measurement unit 1000.

The processor 150 performs signal processing on the stored digital signal so as to generate information on the subject 900 (subject information) to be output to the display unit 190. The display unit 190 displays numerical values and images which are information on the subject 900. A doctor, that is, an operator, checks the numerical values and the images which are information on the subject 900 displayed in the display unit 190 so as to make a diagnosis.

The information on the subject obtained by the photoacoustic apparatus 100 of this embodiment is at least one of a generation sound pressure (an initial sound pressure) of the photoacoustic wave, light absorption energy density, a light absorption coefficient, and information on concentration of a substance included in the subject 900. Examples of the information on concentration of a substance include oxyhemoglobin concentration, deoxyhemoglobin concentration, total hemoglobin concentration, and oxygen saturation. The total hemoglobin concentration is a sum of the oxyhemoglobin concentration and the deoxyhemoglobin concentration. The oxygen saturation is a rate of oxyhemoglobin to total hemoglobin. The photoacoustic apparatus 100 of this embodiment may obtain distribution information (image data) representing values of the information in various positions (various positions in a 2D or 3D space) in the subject or a representative value (a mean value or the like) of the information on the subject 900 as subject information.

Note that the signal data obtained by the photoacoustic measurement is stored, and therefore, different signal processes may be repeatedly performed on the same signal data. Accordingly, even in a case where desired information may not be generated from the signal data since an inappropriate signal process is performed, desired information may be generated by further performing a different signal process. Specifically, desired information may be generated from the signal data without a further burden of the examinee after the photoacoustic measurement is performed.

However, in a case where desired signal data may not be obtained since inappropriate photoacoustic measurement is performed, the examinee is detained again and the photoacoustic measurement is performed again. The repetitive photoacoustic measurement causes a burden of the examinee, and therefore, is preferably avoided.

Here, it is assumed that, in the photoacoustic apparatus 100, different hardware units are used for different examination orders. An examination portion, an examination object, and an examination depth are assumed to be the examination order of the photoacoustic apparatus 100. Note that examples of a diagnosis utilizing the photoacoustic apparatus 100 include a breast cancer diagnosis using oxygen saturation of a blood vessel as an index, a skin cancer diagnosis, such as a melanoma diagnosis, using an amount of melanin in the skin as an index, and a skin aging diagnosis for beauty care using amount of collagen in the skin as an index. The examples of the diagnosis utilizing the photoacoustic apparatus 100 further include a rheumatism diagnosis and a peripheral vascular disease diagnosis using a form of a blood vessel as an index.

According to such a diagnosis utilizing the photoacoustic apparatus 100, various portions (a hand, a leg, a face, a breast, and so on) may be examined. In this case, for example, a preferable shape of the acoustic wave reception unit 120 or preferable element arrangement of a transducer may vary depending on a portion to be examined.

Furthermore, in the diagnosis utilizing the photoacoustic apparatus 100, various objects (a form of a blood vessel, oxygen saturation in a blood vessel, an amount of collagen in the skin, an amount of melanin in the skin, and so on) may be examined. Furthermore, different examination objects which serve as a sound source of a photoacoustic wave may have different sizes. On the other hand, in general, a frequency spectrum of the photoacoustic wave to be generated varies depending on a size of the sound source. Furthermore, if an object to be examined is determined, a resolution required for a diagnosis of the object to be examined is also determined. Therefore, it is preferable that a frequency component which is included a lot in a photoacoustic wave generated from an examination substance of the object to be examined is sufficiently received and signal data which satisfies a required resolution is collected. Accordingly, a preferable reception band of the acoustic wave reception unit 120 may vary depending on the object to be examined. Furthermore, a preferable sampling frequency of AD conversion in the signal data collection unit 130 and a preferable frequency filter for an analog signal may vary depending on the object to be examined.

Furthermore, in the diagnosis utilizing the photoacoustic apparatus 100, an absorption coefficient spectrum for a light wavelength varies depending on an inspection substance serving as the object to be examined, and an efficiency of generation of a photoacoustic wave varies depending on a wavelength of irradiation light. Therefore, a preferable wavelength and a preferable intensity of light emitted from the light irradiation unit 110 may vary depending on the object to be examined.

In the diagnosis utilizing the photoacoustic apparatus 100, a region of interest (ROI) serving as an examination range may be arbitrarily set. Here, rates of intensities of light which reaches various positions in the subject to an intensity of incident light vary from one another. Therefore, to sufficiently ensure a generation sound pressure of photoacoustic waves, a preferable light intensity and a preferable wavelength of the light emitted from the light irradiation unit 110 may vary depending on an examination depth. Here, the examination depth means a position which is farthest from a light irradiation position in the set ROI. Typically, an intensity of light which reaches this position is the lowest.

As described above, in the photoacoustic apparatus 100, the relationships between the examination orders and hardware units suitable for the examination orders are complicated. Therefore, it may be difficult for the operator to check whether preferable hardware units are connected to the examination orders. However, to avoid remeasurement of photoacoustic waves, it is required to be determined whether the photoacoustic measurement unit 1000 currently provided is constituted by a hardware unit suitable for the examination order. Therefore, an operational efficiency of the examination utilizing the photoacoustic apparatus 100 may be degraded.

Accordingly, the photoacoustic apparatus 100 of this embodiment notifies the operator of a result of the determination as to whether the examination order and a provided hardware unit match each other. The photoacoustic apparatus 100 of this embodiment determines whether a hardware unit included in the photoacoustic measurement unit 1000 is suitable for the examination order, and notifies the operator of a result of the determination. Specifically, the photoacoustic apparatus 100 of this embodiment determines whether a hardware unit suitable for the examination order has been connected to the processor and notifies the operator of a result of the determination. By this, the operator may easily recognize whether a hardware unit suitable for the examination order has been provided, and accordingly, the operational efficiency of the examination is improved.

Figure 2:
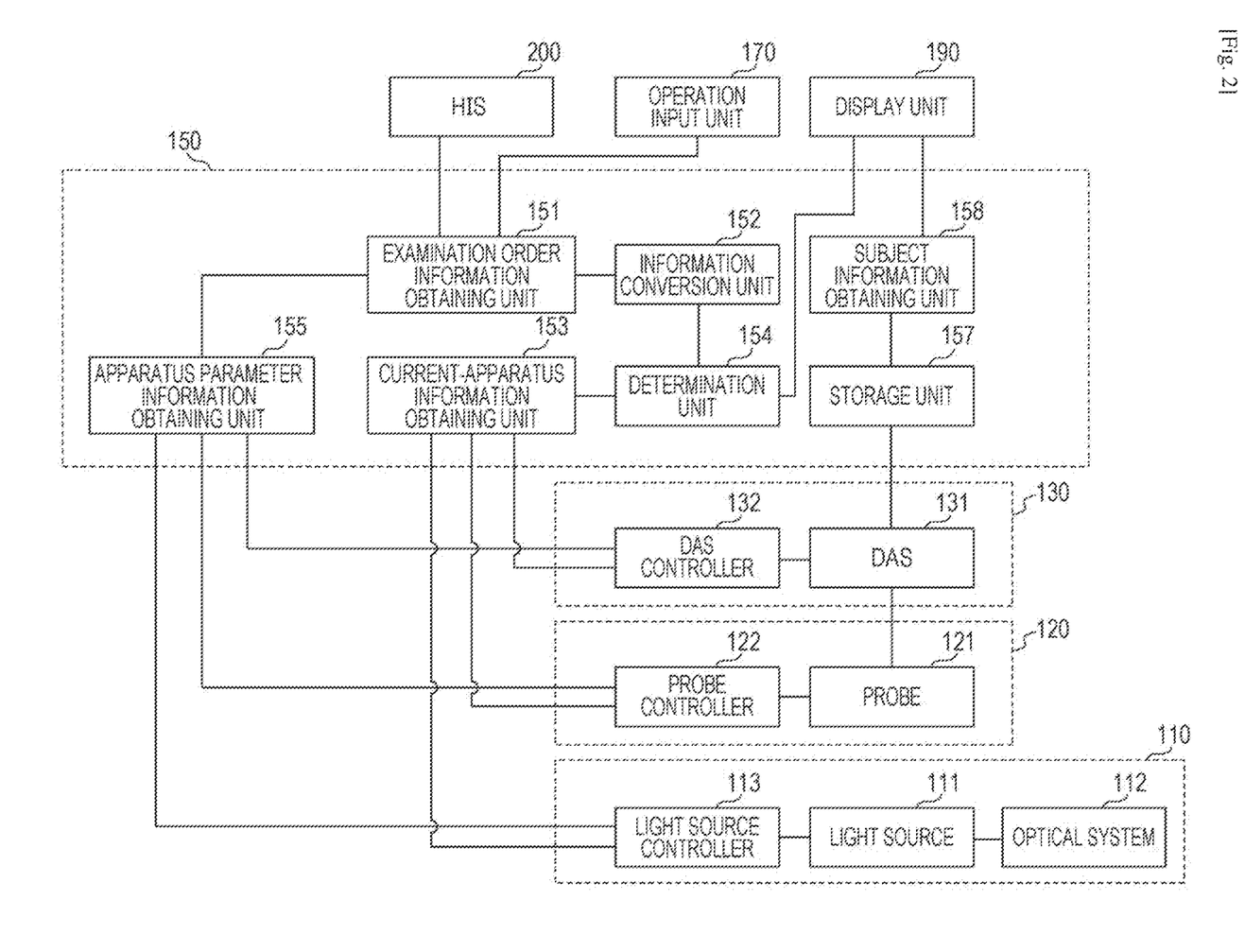
FIG. 2 is a block diagram illustrating a photoacoustic apparatus according to the embodiment in detail.

FIG. 2 is a block diagram illustrating the photoacoustic apparatus 100 according to this embodiment in detail. Components will be described in detail hereinafter.

Light Irradiation Unit 110

The light irradiation unit 110 includes a light source 111 which emits light, an optical system 112 which guides the light emitted from the light source 111 to the subject 900, and a light source controller 113 which controls the light source 111.

The light emitted from the light source 111 may have a pulse width in a range from 1 ns or more to 100 ns or less. Furthermore, the light emitted from the light source 111 may have a wavelength in a range from approximately 400 nm to approximately 1600 nm. In a case where a blood vessel in the vicinity of a surface of a living body is to be imaged with high resolution, a wavelength which is considerably absorbed by the blood vessel (in a range from 400 nm or more to 700 nm or less) may be employed. On the other hand, in a case where a depth portion of the living body is to be imaged, light having a wavelength (in a range from 700 nm or more to 1100 nm or less) which is typically less absorbed by a background tissue of the living body (water, fat, or the like) may be used.

As the light source 111, laser or a light emitting diode may be used. Furthermore, in a case where measurement is performed using light having a plurality of wavelengths, a light source capable of changing a wavelength may be used. Note that, in a case where the subject is irradiated with light having a plurality of wavelengths, a plurality of light sources which generate light of different wavelengths may be provided and irradiation may be performed in turn from the light sources. Even in the case where a plurality of light sources are used, the plurality of light sources are collectively referred to as a light source. Examples of the laser include a solid-state laser, a gas laser, a dye laser, and a semiconductor laser. In particular, a pulse laser, such as an Nd:YAG laser or an alexandrite laser, is preferably used. Alternatively, a Ti:sa laser using Nd:YAG laser light as excitation light or an optical parametric oscillator (OPO) laser may be used.

As the optical system 112, an optical element, such as a lens or a mirror, may be employed. Furthermore, as the optical system 112, a spatial propagation unit utilizing an articulated arm using a reflection mirror or prism or a light propagation unit utilizing a fiber or a bundle fiber may be used. Furthermore, a portion of the light may be separated using a beam splitter or the like so that information on incident light, such as light irradiation energy or an irradiation distribution measurement, is collected.

Assuming that the subject 900 is a breast, a light emission unit of the optical system 112 may be constituted by a diffuser plate or the like which diffuses light so as to emit pulse light with an increased beam diameter. On the other hand, in a photoacoustic microscope, the light emission unit of the optical system 112 may be constituted by a lens or the like so as to emit a focused beam so that an improved resolution is obtained.

A light irradiation position on the subject 900 may be movable. In this case, in addition to a method for directly moving the articulated arm and the fiber relative to the subject 900, a method using a movable mirror or the like, a method for mechanically moving a light source, or the like may be employed.

Note that the light irradiation unit 110 may not include the optical system 112 and the light source 111 may directly irradiate the subject 900 with light.

The light source controller 113 may control apparatus parameters (including a wavelength, a pulse width, and an output) of the light source 111. Specifically, the light source controller 113 may control driving of the light source 111 so as to change a characteristic of light emitted from the light source 111. Furthermore, the light source controller 113 may transmit a hardware ID (a light source ID) assigned to the light source 111 as current-apparatus information to the processor 150. Moreover, the light source controller 113 may transmit a parameter of light which may be emitted from the connected light source 111, that is, information on a specification of the light source 111, as the current-apparatus information to the processor 150. Note that the light source controller 113 has a plurality of connection slots serving as connection units so that a plurality of light sources 111 may be connected to the light source controller 113.

Acoustic Wave Reception Unit 120

The acoustic wave reception unit 120 includes a probe 121 which outputs an electric signal in response to a received acoustic wave and a probe controller 122 which controls the probe 121.

The probe 121 includes a transducer which converts an acoustic wave into an electric signal. Furthermore, the probe 121 may include a processing circuit which processes an analog signal output from the transducer depending on a type of the transducer. The transducer may be formed of a piezoelectric ceramic member typified by lead zirconate titanate (PZT) or a macromolecular piezoelectric membrane member typified by polyvinylidene fluoride (PVDF). Furthermore, a capacitive micro-machined ultrasonic transducer (CMUT) or a transducer using a Fabry-Perot interferometer may be used as the transducer. Note that any transducer may be employed as long as the transducer is capable of outputting an electric signal in response to a received acoustic wave. The probe 121 may include a plurality of transducers. Furthermore, the plurality of transducers included in the probe 121 may be arranged in a one-dimensional manner or a two-dimensional manner. Moreover, the plurality of transducers included in the probe 121 may be arranged in a three-dimensional manner. For example, the plurality of transducers may be arranged in a hemispherical shape.

The probe controller 122 may control the apparatus parameters of the probe 121. In a case where the CMUT is used as the transducer included in the probe 121, for example, a voltage applied to the CMUT or the like corresponds to the apparatus parameter of the probe 121. Note that, in a case where a piezoelectric member is used as the transducer included in the probe 121, the probe controller 122 may not set the apparatus parameter of the probe 121. Furthermore, the probe controller 122 may transmit a hardware ID (a probe ID) assigned to the probe 121 as current-apparatus information to the processor 150. Moreover, the probe controller 122 may transmit information on a receivable frequency band of the probe 121 currently connected, that is, information on a specification of the probe 121, as the current-apparatus information the processor 150. Note that the probe controller 122 may have a plurality of connection slots serving as connection units to which a plurality of probes 121 are to be connected.

Signal Data Collection Unit 130

The signal data collection unit 130 includes a data acquisition system (DAS) 131 which converts the analog electric signal output from the probe 121 into a digital signal and a data acquisition system (DAS) controller 132 which controls the DAS 131. The DAS 131 typically includes an amplifier which amplifies the analog electric signal output from the probe 121, a frequency filter which allows a specific frequency component included in the analog signal to pass, and an A/D converter which converts the analog signal into a digital signal. The digital signal output from the signal data collection unit 130 is stored in a storage unit 157 included in the processor 150.

A DAS controller 132 may control apparatus parameters of the DAS 131. Examples of the apparatus parameters of the DAS 131 include a sampling frequency of AD conversion (a clock signal applied to the A/D converter). Furthermore, the DAS controller 132 may transmit a hardware ID (a DAS ID) assigned to the DAS 131 as current-apparatus information to the processor 150. Moreover, the DAS controller 132 may transmit information on a range of a sampling frequency and information on a range of a frequency filter which are changeable by the DAS 131 which is currently connected, that is, information on a specification of the DAS 131, as the current-apparatus information to the processor 150. Note that the DAS controller 132 may have a plurality of connection slots so that the plurality of DASs 131 may be connected to the DAS controller 132.

Processor 150

The processor 150 includes an examination order information obtaining unit 151, an information conversion unit 152, a current-apparatus information obtaining unit 153, a determination unit 154, an apparatus parameter information obtaining unit 155, the storage unit 157, and a subject information obtaining unit 158. Functions of the components will be described when a processing flow is described.

Units which have a calculation function of the examination order information obtaining unit 151, the information conversion unit 152, the current-apparatus information obtaining unit 153, the determination unit 154, the apparatus parameter information obtaining unit 155, the subject information obtaining unit 158, and the like may be configured by a processor, such as a CPU or a graphics processing unit (GPU) or a calculation circuit, such as a field programmable gate array (FPGA) chip. Each of these units may be configured by a single processor or a single calculation circuit, and may be configured by a plurality of processors or a plurality of calculation circuits.

The storage unit 157 may be constituted by a non-transitory storage medium, such as a magnetic disk or a flash memory. The storage unit 157 may be a volatile medium, such as a dynamic random access memory (DRAM). Note that the storage medium which stores programs is a non-transitory storage medium.

The processor 150 may be a dedicatedly-designed work station. Furthermore, the components of the processor 150 may be configured by different hardware units. At least some of the configurations included in the processor 150 may be constituted by a single hardware unit. The functions of the processor 150 may be realized by hardware which physically exists in a remote location.

Operation Input Unit 170

The operation input unit 170 may be constituted by a mouse or a keyboard to be operated by the operator. The display unit 190 may be constituted by a touch panel so as to serve as the operation input unit 170.

Display Unit 190

The display unit 190 is a liquid crystal display, an organic electro luminescence display, or the like. The display unit 190 displays an image based on the subject information obtained by the processor 150, a numerical value of a specific position, and the like on a screen. The display unit 190 may display graphic user interfaces (GUIs) for operating images and the apparatus on the screen.

Note that the components included in the photoacoustic apparatus 100 may be configured as different devices or an integrated single device. Specifically, at least two of the light irradiation unit 110, the acoustic wave reception unit 120, the signal data collection unit 130, the processor 150, the operation input unit 170, and the display unit 190 may be accommodated in the same case.

Furthermore, a plurality of components may be set as one unit, and each unit may be connected to a connection slot serving as a connection unit. For example, the light irradiation unit 110, the acoustic wave reception unit 120, and the signal data collection unit 130 may be accommodated in one case as one unit to be connected to a connection slot.

The photoacoustic apparatus 100 may include a holding unit which holds a shape of the subject 900 in the measurement. The holding unit may be formed of PET-G or the like. The holding unit is preferably formed of material having a degree of hardness for holding the subject 900. The holding unit may be formed of material which allows light to be used in the measurement to pass. The holding unit may be formed of material having impedance similar to that of the subject 900. In a case where a portion having a curved surface, such as a breast, is set as the subject 900, the holding unit may have a concave shape. In this case, the subject 900 may be inserted into a concave portion of the holding unit.

Figure 3:
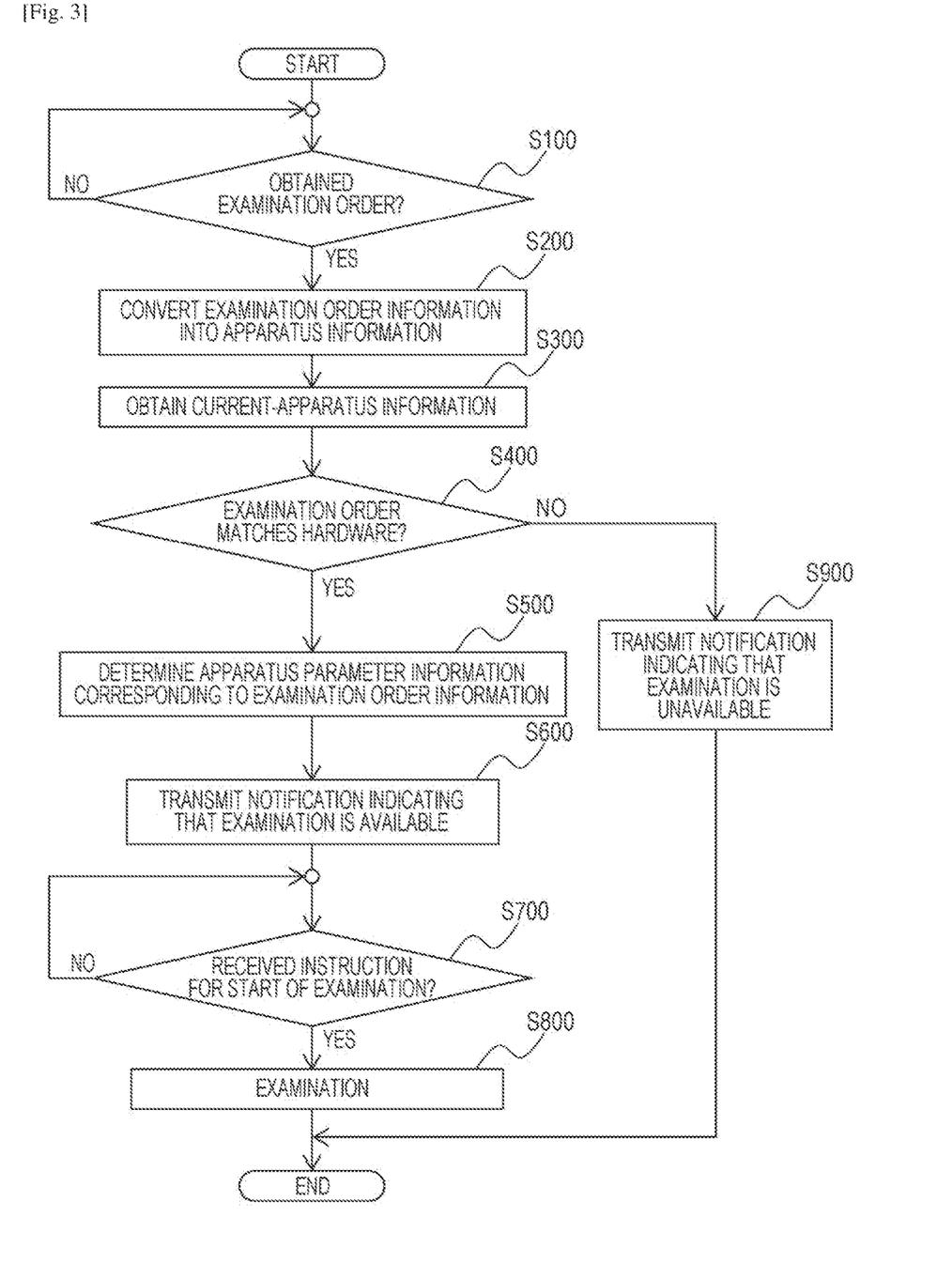
FIG. 3 is a flowchart illustrating a process according to the embodiment.
Figure 4:
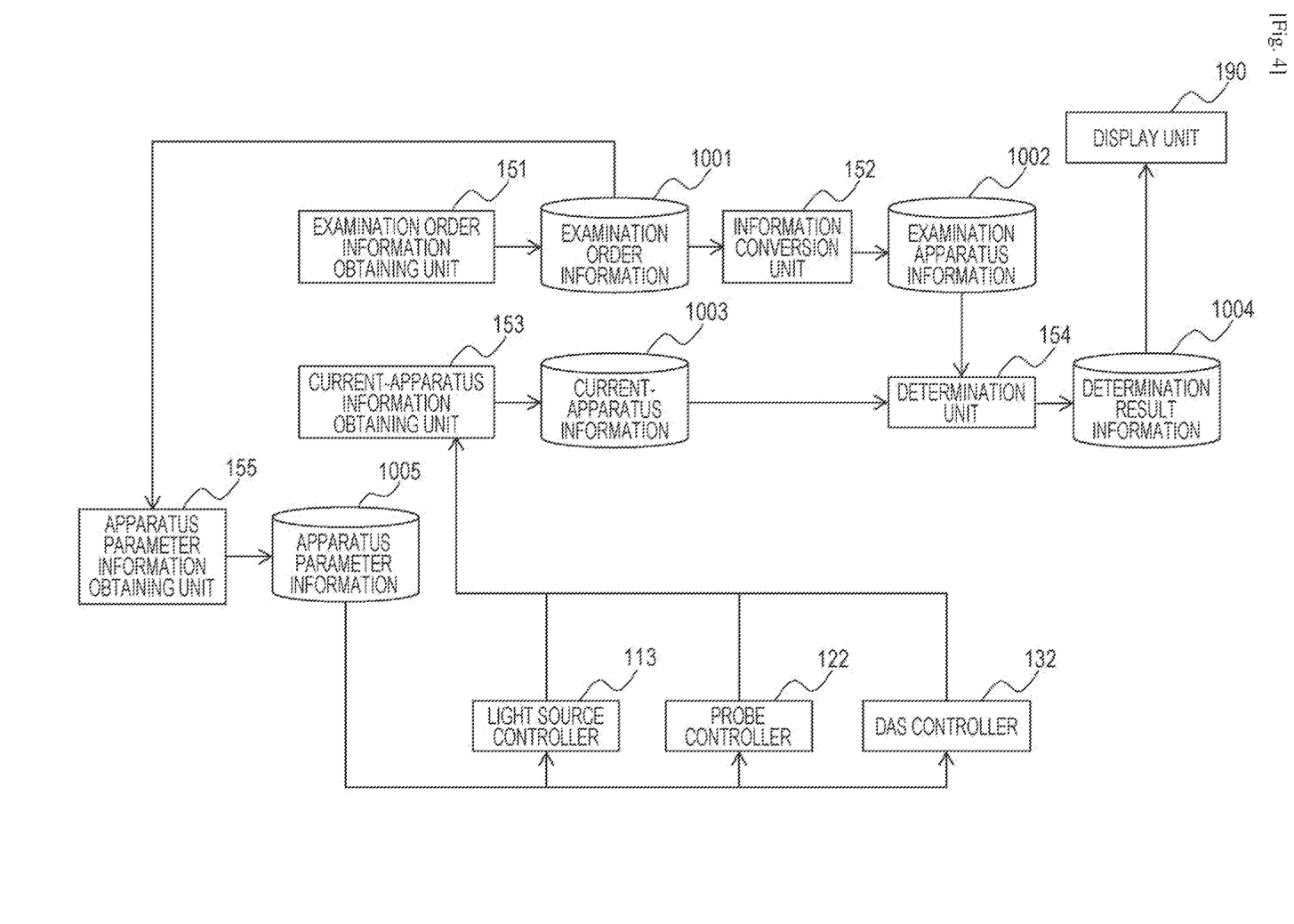
FIG. 4 is a diagram illustrating a data flow according to the embodiment.

Next, a flowchart of a process including an examination support method performed after the photoacoustic apparatus 100 according to this embodiment receives an examination order will be described with reference to FIG. 3. FIG. 4 is a data flow according to this embodiment. In this embodiment, a case where a hardware ID assigned to the apparatus is employed as the apparatus information will be described.

Step S100: Process of Determining Whether Examination Order has been Obtained

The examination order information obtaining unit 151 serving as a first obtaining unit waits for a reception of an examination order. When receiving examination order information 1001, the examination order information obtaining unit 151 transmits the examination order information 1001 to the information conversion unit 152 and the process proceeds to step S200. Alternatively, the examination order information obtaining unit 151 may transmit the examination order information 1001 to the display unit 190 so that the display unit 190 displays the examination order information 1001.

The examination order information obtaining unit 151 may obtain the examination order information 1001 by receiving an examination order transmitted from the HIS 200 through a network, such as the Ethernet (registered trademark), or by receiving an examination order input by the operator using the operation input unit 170. As described above, the examination order of the photoacoustic apparatus 100 includes an examination portion, an examination target, and an examination depth, in addition to an examinee ID, an examination ID, and an imaging date and time. The examination order of this embodiment includes at least one of items, that is, one of the examination portion, the examination target, and the examination depth. Note that the examination order may be a list including examination orders of a plurality of examinees.

Figure 5:
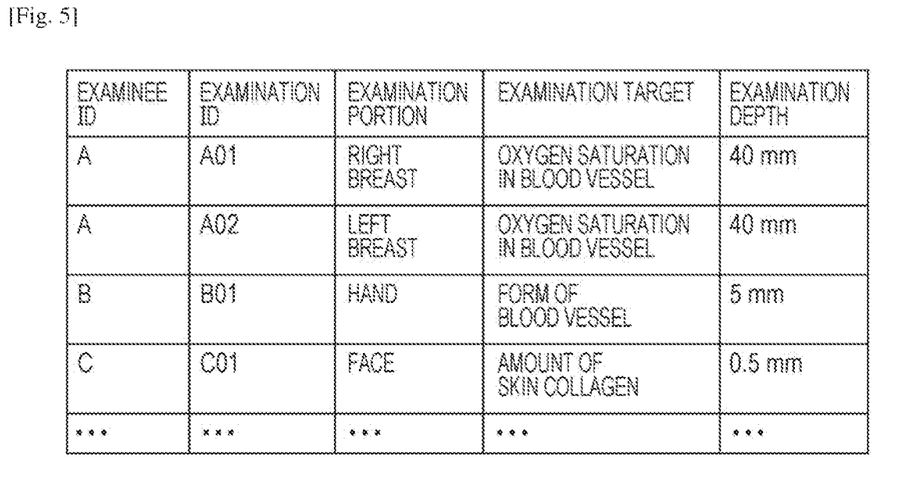
FIG. 5 is a diagram illustrating examination orders according to the embodiment.

FIG. 5 is a diagram illustrating the examination order information 1001 according to this embodiment. As illustrated in FIG. 5, an examination portion, an examination target, and an examination depth are set for each examination ID.

Step S200: Process of Converting Examination Order Information into Apparatus Information The information conversion unit 152 receives the examination order information 1001 transmitted from the examination order information obtaining unit 151 and converts the examination order information 1001 into examination apparatus information 1002 required for the examination. Specifically, the information conversion unit 152 serving as the first obtaining unit obtains the examination apparatus information 1002 as first apparatus information using the examination order information 1001. The information conversion unit 152 converts the examination order information 1001 into the examination apparatus information 1002 with reference to a correspondence table indicating the correspondences between the hardware IDs serving as the examination apparatus information 1002 and the items of the examination order.

Figure 6A:
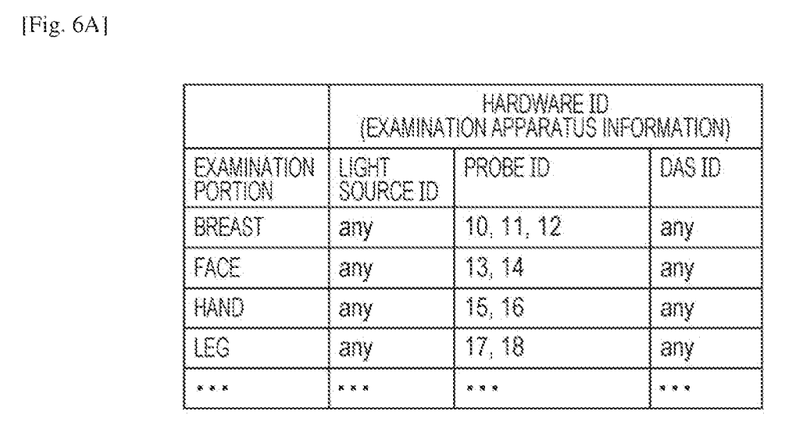
FIG. 6A is a diagram illustrating a table of correspondences between examination orders and hardware IDs according to the embodiment.
Figure 6B:
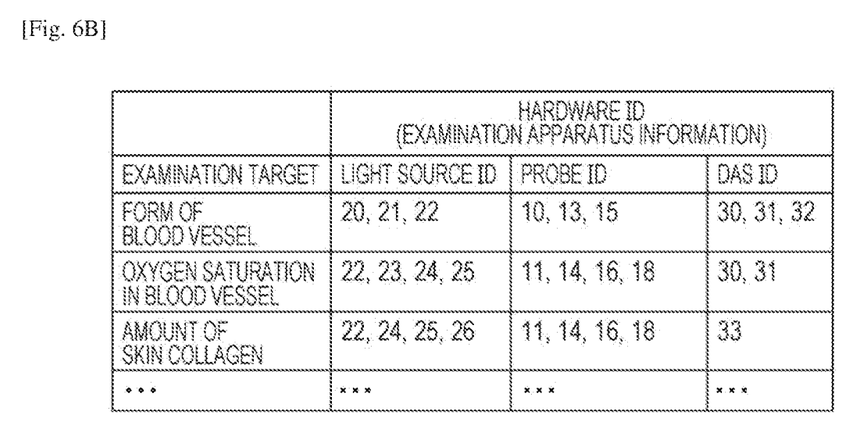
FIG. 6B is a diagram illustrating a table of correspondences between examination orders and hardware IDs.

FIGS. 6A and 6B are tables of correspondence between the examination order information 1001 and the examination apparatus information 1002 in this embodiment. In FIGS. 6A and 6B, the correspondence tables indicating the correspondences between the items of the examination orders and the hardware IDs assigned to the components included in the photoacoustic apparatus 100 are illustrated. FIG. 6A is a correspondence table indicating the correspondences between examination portions and hardware IDs assigned to the light source 111, the probe 121, and the DAS 131. As described above, a preferable reception band of the probe 121 varies depending on an examination portion, and therefore, the different examination portions are associated with different probe IDs. Note that, in this embodiment, the correspondence tables are provided on the assumption that preferable conditions of the light source 111 and the DAS 131 do not vary depending on an examination portion. Specifically, the light source 111 and the DAS 131 have any hardware ID and correspond to any examination portion. Note that a correspondence table in which an examination portion is associated with the light source 111 and the DAS 131 may be provided.

Furthermore, FIG. 6B is a correspondence table indicating correspondences between examination targets and hardware IDs assigned to the light source 111, the probe 121, and the DAS 131. Even in a case where a preferable wavelength varies depending on an examination target, if a light source may change a wavelength, the light source may be used for various examination targets. As illustrated, the light source 111 having a light source ID 22 may be used for different examination targets. The same is true to the other preferable parameters. As for the probe 121 and the DAS 131, one probe may be used for different examination targets.

Similarly, a correspondence table indicating correspondences between other examination orders, such as the examination depth, and hardware IDs of the hardware units is provided.

Step S300: Process of Obtaining Current-Apparatus Information

The current-apparatus information obtaining unit 153 serving as a second obtaining unit obtains apparatus information of the hardware units connected to the connection slots and included in the photoacoustic measurement unit 1000 as second apparatus information. Furthermore, the apparatus information of the hardware units connected to the connection units and included in the photoacoustic measurement unit 1000 is also referred to as "current-apparatus information". In this embodiment, the current-apparatus information obtaining unit 153 transmits a control signal to the light source controller 113, the probe controller 122, and the DAS controller 132 so that the controllers transmit the hardware IDs (current-apparatus information) assigned to the hardware units which are currently connected to the controllers. The controllers which have received the control signal read the hardware IDs of the hardware units corresponding to the controllers and transmit the hardware IDs to the current-apparatus information obtaining unit 153. The current-apparatus information may be transmitted and received through a general serial communication, such as RS232 or a USB. Furthermore, the current-apparatus information obtaining unit 153 may obtain current-apparatus information 1003 by reading barcodes attached to the hardware units included in the photoacoustic measurement unit 1000. In this case, the current-apparatus information obtaining unit 153 may include a barcode reader. Note that the term "connection" includes wired connection and wireless connection.

Although the case where the process in step S300 is executed after the examination order is received in step S100 has been described, the current-apparatus information 1003 may be constantly updated. Specifically, the process in step S300 may be executed before the process in step S100.

Note that the current-apparatus information obtaining unit 153 may display the current-apparatus information of the hardware units in the display unit 190. Furthermore, in a case where each of the controllers includes a plurality of connection slots, the relationships between the connection slots and hardware units may be displayed in the display unit 190.

Moreover, the photoacoustic apparatus 100 may include an input unit including buttons corresponding to the connection slots, and the operator may press one of the buttons corresponding to one of the connection slots connected to the photoacoustic measurement unit 1000 to be used, so that the photoacoustic measurement unit 1000 which is a target of a determination of match with the examination order is selected. Furthermore, the photoacoustic measurement unit 1000 connected to the connection slot may be displayed in the display unit so that the operator selects the photoacoustic measurement unit 1000 to be used using the GUI.

Step S400: Process of Determining Whether Hardware Unit is Suitable for Examination Order The determination unit 154 receives a hardware ID serving as the examination apparatus information 1002 from the information conversion unit 152 and a hardware ID serving as the current-apparatus information 1003 from the current-apparatus information obtaining unit 153 and compares the IDs so as to determine whether the IDs match each other (coincide with each other). In a case where the hardware IDs of the light source 111, the probe 121, and the DAS 131 which are currently connected match hardware IDs requested in the examination, the process proceeds to step S500. On the other hand, the hardware IDs do not match, the process proceeds to step S900.

Figure 7:
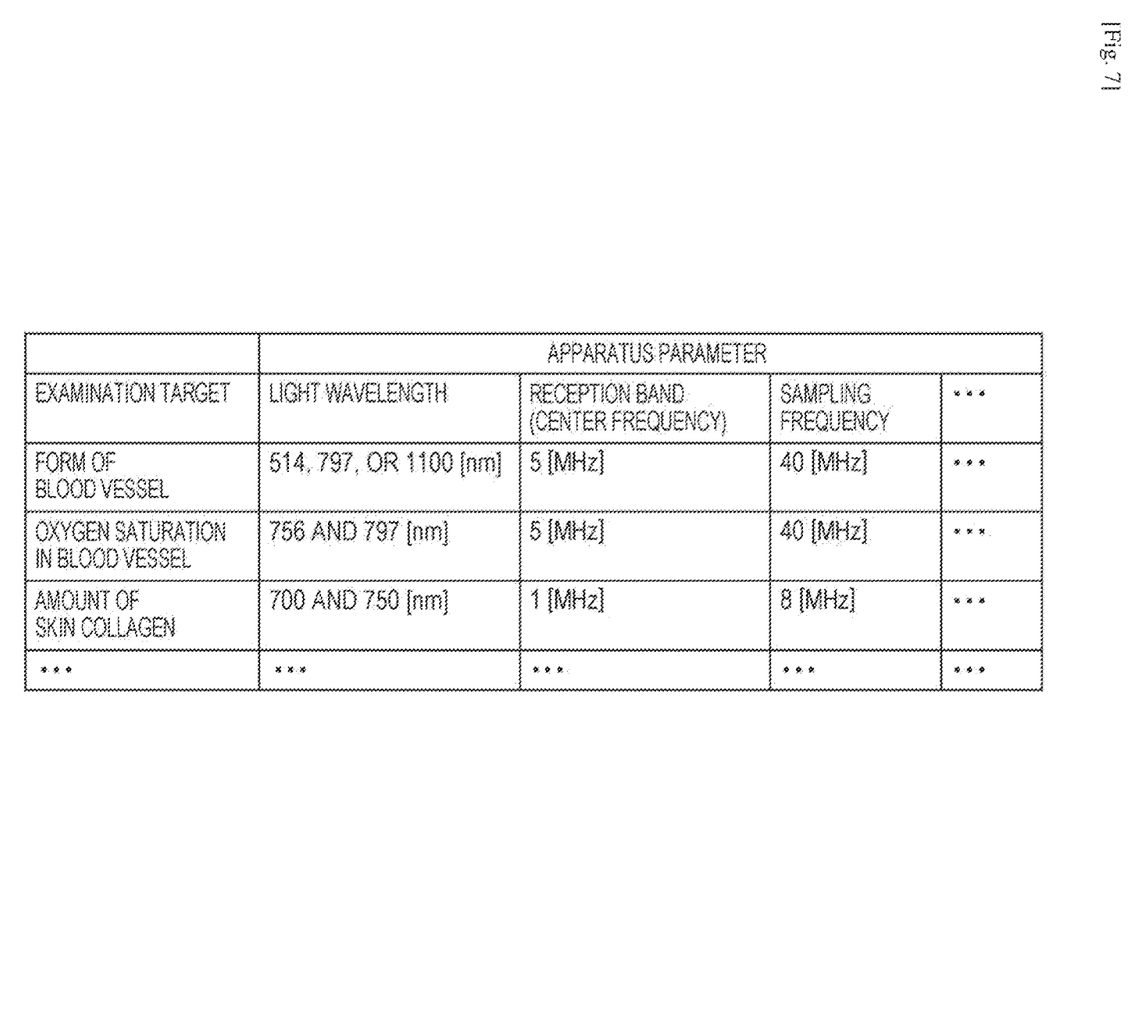
FIG. 7 is a diagram illustrating a table of correspondences between examination orders and apparatus parameters.

Step S500: Process of Obtaining Apparatus Parameter Information which Matches Examination Order Information The apparatus parameter information obtaining unit 155 determines apparatus parameter information 1005 of the hardware units included in the photoacoustic measurement unit 1000 in accordance with the examination order information 1001. Specifically, the apparatus parameter information obtaining unit 155 determines apparatus parameters required for the examination based on the examination order. In this embodiment, the apparatus parameter information obtaining unit 155 obtains information on an optical parameter, information on a reception band, information on a sampling frequency, information on a frequency filter, and the like required for the examination as the apparatus parameter information 1005 in accordance with the examination order information 1001. Note that the apparatus parameter information obtaining unit 155 may convert the examination order information 1001 into the apparatus parameter information 1005 with reference to a correspondence table including the correspondences between the items of the examination order and the apparatus parameters required for the examination. FIG. 7 is a correspondence table between the examination order information 1001 and the apparatus parameter information 1005 in this embodiment. In FIG. 7, an example of a correspondence table representing the correspondences between examination targets serving as the examination order information 1001 and light wavelengths, reception bands, and sampling frequencies which serve as the apparatus parameter information 1005 is illustrated. As illustrated in FIG. 7, a light wavelength may be selected from among a plurality of options when a form of a blood vessel is to be examined. In this case, a wavelength which satisfies all the apparatus parameters required for light wavelengths of other examination orders is obtained as the apparatus parameter information 1005. Furthermore, as illustrated in FIG. 7, in a case where information obtained by a spectrum, such as oxygen saturation or an amount of collagen, is to be examined, emission of light having two or more wavelengths may be required. Meanwhile, a generation available wavelength band and a gain efficiency for each wavelength vary depending on a type of the light source. Therefore, in a case where a plurality of light sources are connected, a measurement unit having one of the light sources in which a light wavelength required for the examination order matches a light wavelength serving as an apparatus parameter of the light source is preferably determined.

Figure 8:
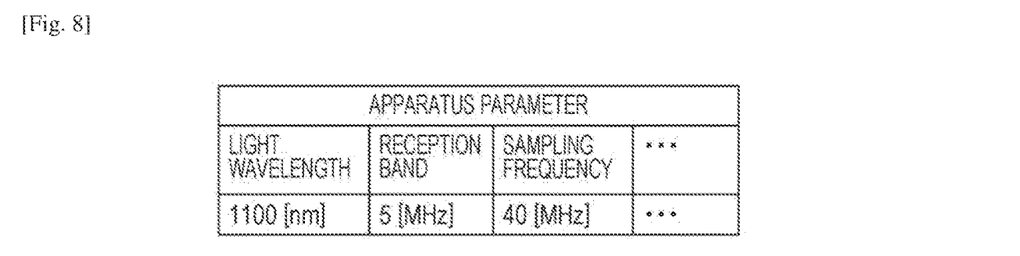
FIG. 8 is a diagram illustrating a table of apparatus parameters according to the embodiment.

FIG. 8 is a diagram illustrating the apparatus parameter information 1005 obtained by the apparatus parameter information obtaining unit 155. In FIG. 8, an examination ID indicates an apparatus parameter corresponding to an examination order of A01.

Step S600: Process of Performing Notification Indicating that Examination is Available The display unit 190 serving as a notification unit receives determination result information 1004 indicating that match of the hardware IDs from the determination unit 154 and displays information indicating that the examination is available. For example, the display unit 190 displays information indicating that examination is available by displaying a character string "EXAMINATION AVAILABLE" or by enabling an icon for issuing an instruction for start of examination. The notification method is not limited to the method of displaying a result of the determination in the display unit 190 for notification for the operator, and the examination available state may be notified through a speaker by sound. Furthermore, the notification indicating that the examination is available may be made by turning on or off a display lamp, such as an LED lamp, attached to the photoacoustic apparatus 100 or by changing a color of the display lamp. In this case, the speaker or the display lamp serves as the notification unit. Furthermore, any method may be employed in the notification as long as the operator notices the determination result.

S700: Process of Determining Whether Examination Start Instruction has been Received A main controller (not illustrated) constituted by a CPU and the like waits for a reception of an examination start instruction. When the operator issues an examination start instruction using the operation input unit 170, the main controller receives the examination start instruction. Then the process proceeds to step S800.

Step S800: Examination Process

When receiving the examination start instruction, the main controller transmits a control signal which causes an examination performed on the components included in the photoacoustic apparatus 100. The photoacoustic apparatus 100 performs an examination in response to the instruction issued by the main controller. Here, the main controller reads a program code stored in the storage unit 157 and controls operations of the components included in the photoacoustic apparatus 100.

The controllers which receive the examination start instruction set the apparatus parameters illustrated in FIG. 8 to the hardware units of the photoacoustic measurement unit 1000. For example, the light source controller 113 sets a wavelength of light emitted from the light source 111 to 1100 nm with reference to the apparatus parameter information illustrated in FIG. 8. Furthermore, in a case where the light source controller 113 determines that emission of light having a plurality of wavelengths is required based on the examination order information 1001, a plurality of wavelengths of the light emitted from the light source 111 is set. The controllers set the other apparatus parameters with reference to the table.

When the photoacoustic apparatus 100 receives the examination start instruction, the photoacoustic measurement unit 1000 irradiates the subject 900 with light and outputs signal data derived from an acoustic wave (a photoacoustic wave) generated by the light irradiation. The signal data output from the photoacoustic apparatus 100 is stored in the storage unit 157. The subject information obtaining unit 158 obtains subject information using the signal data stored in the storage unit 157. Note that, as a method for obtaining subject information from signal data, a general reconfiguration method, such as a time-domain reconfiguration method, a Fourier domain reconfiguration method, or a model base reconfiguration method (a repeat reconfiguration method), may be used. For example, a time domain reconfiguration method which is referred to as universal back-projection (UBP) may be employed as disclosed in PHYSICAL REVIEW E 71,016706 (2005). The subject information obtaining unit 158 outputs the subject information to the display unit 190 so as to display numerical values and images associated with the subject information in the display unit 190.

Note that a storage controller of the processor 150 may store the obtained subject information and the examination order information 1001 received to obtain the subject information which are associated with each other in the storage unit 157. When the operator reads the subject information from the storage unit 157 to be checked in the display unit 190 after the examination, the examination order information 1001 which is stored in association with the subject information may be also read from the storage unit 157 and checked.

Step S900: Process of Performing Examination Unavailable Notification

The display unit 190 serving as the notification unit receives the determination result information 1004 indicating mismatch of the hardware IDs from the determination unit 154 and displays information indicating that the examination is unavailable. For example, the display unit 190 displays information indicating that the examination is unavailable by displaying a character string "EXAMINATION UNAVAILABLE" or by disabling an icon for issuing an instruction for start of the examination displayed in the display unit 190. The notification method is not limited to a method of displaying the determination result in the display unit 190 for notification for the operator, and the notification of an examination unavailable state may be performed through a speaker by sound. Furthermore, the notification indicating that the examination is unavailable may be performed by turning on or off the display lamp attached to the photoacoustic apparatus 100 or by changing a color of the display lamp. Note that the display lamp may be turned on in the examination available state and turned off in the examination unavailable state for the notification for the operator. Furthermore, the relationship between turning-on and turning-off of the lamp may be reversed. Note that different colors may be used in different states of the display lamp, that is, the examination available state and the examination unavailable state, for the notification for the operator. Note that any configuration may be employed in the notification unit as long as the operator may recognize whether the examination order information 1001 matches the current-apparatus information 1003.

In the process in step S900, the main controller may be configured such that the operator may not instruct a start of the examination using the operation input unit 170. Specifically, the main controller may be configured such that an instruction for starting the examination issued by the operator is accepted after the process in step S600 is completed.

By this, the operator may easily recognize whether the hardware units currently provided match the examination order. Only when the hardware units do not match the examination order, the operator checks hardware IDs and replaces a hardware unit having a hardware ID which does not match the examination order by a hardware unit having a hardware ID which matches the examination order to be connected. By this, the operational efficiency of the examination may be improved.

Furthermore, the notification unit may make a notification indicating a hardware unit which does not match the examination order. Specifically, the notification unit may make a notification indicating information on a hardware ID of the hardware unit which does not match the examination order, information on a hardware name (the light source 111, the probe 121, the DAS 131, or the like) of the hardware unit which does not match the examination order, and the like. By this, when a notification indicating that the examination is unavailable is performed, the operator is not required to perform a determination as to whether a hardware unit matches the examination order on all the hardware units. The operator replaces the notified hardware unit by a hardware unit which matches the examination order.

Furthermore, the notification unit may perform a notification indicating a hardware ID suitable for the examination order instead of the hardware unit having the mismatch hardware ID. Since the operator merely connects the hardware unit having the notified hardware ID, a period of time required for discussing a hardware ID suitable for the examination order may be reduced.

Although the case where a hardware ID is employed as the apparatus information is described in the foregoing example, specification information of the photoacoustic measurement unit 1000 or apparatus parameter information required for the examination may be employed as the apparatus information.

In this case, as with the process in step S500, the information conversion unit 152 obtains the apparatus parameter information 1005 required for the examination as the examination apparatus information 1002 in accordance with the examination order information in step S200. In addition, the obtained examination apparatus information 1002 may be used as the apparatus parameter information 1005. Therefore, the apparatus parameter information 1005 may be determined without executing the process in step S500. Specifically, the information conversion unit 152 may function as the apparatus parameter information obtaining unit 155.

Furthermore, the current-apparatus information obtaining unit 153 obtains the specification information of the photoacoustic measurement unit 1000 as the current-apparatus information 1003 in step S300. The current-apparatus information obtaining unit 153 obtains the current-apparatus information 1003 of the hardware units included in the provided photoacoustic measurement unit 1000. In this embodiment, the current-apparatus information obtaining unit 153 transmits a control signal to the light source controller 113, the probe controller 122, and the DAS controller 132 so that the light source controller 113, the probe controller 122, and the DAS controller 132 transmit information on specifications of the hardware units currently connected to the respective controllers. The controllers which have received the control signal read the corresponding hardware specification information to be transmitted to the current-apparatus information obtaining unit 153.

Furthermore, in step S400, the determination unit 154 determines whether the examination apparatus information 1002 required for the examination matches the current-apparatus information 1003 of the photoacoustic measurement unit 1000. Specifically, the determination unit 154 determines whether the current-apparatus information 1003 of the photoacoustic measurement unit 1000 satisfies the examination apparatus information 1002 required for the examination. If specifications of the hardware units included in the photoacoustic measurement unit 1000 include the apparatus parameters required for the examination, it may be determined that the current-apparatus information 1003 matches the apparatus parameter information 1005.

Furthermore, in step S800, the controllers sets apparatus parameters represented by the examination apparatus information 1002 as apparatus parameter information to the hardware units.

Note that, in a case where the photoacoustic measurement unit 1000 is configured by hardware units which support any examination order or a case where detachment of the hardware units included in the photoacoustic measurement unit 1000 is not assumed, the correspondences between the examination order and the hardware units may not be checked. In this case, the controllers may set the apparatus parameters of the hardware units included in the photoacoustic measurement unit 1000 in accordance with the apparatus parameter information 1005 without performing a notification of a result of the determination of the correlations between the examination order and the hardware units.

Furthermore, in a case where a plurality of photoacoustic measurement units are connected, it may be determined whether an examination order and photoacoustic measurement units 1000 match each other. In this case, a notification controller causes the notification unit to perform a notification indicating one of the plurality of photoacoustic measurement units 1000 which is suitable for the examination order. For example, the photoacoustic measurement unit 1000 may include the notification unit, such as an LED lamp, and the notification controller may perform a notification of a determination result by a method for turning on the LED lamp attached to the photoacoustic measurement unit 1000 which is suitable for the examination order.

Other Embodiments

The present invention may also be realized by executing a process described below. Specifically, software (a program) which realizes the functions of the foregoing embodiment is supplied to a system or an apparatus through a network or various storage medium, and a computer (or a CPU, an MPU, or the like) of the system or the apparatus reads and executes the program.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions, may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-170600, filed Aug. 31, 2015, which is hereby incorporated by reference herein in its entirety.

The invention claimed is:

1. An apparatus comprising:
a memory storing a program; and
one or more processors which, by executing the program, functions as:
a connection unit configured to be able to connect to a plurality of measurement units each of which includes a light irradiation unit which irradiates a subject with light and a reception unit which receives an acoustic wave generated from the subject irradiated with the light;
a first obtaining unit configured to obtain first information on an examination order;
a second obtaining unit configured to obtain second information on a light irradiation unit and third information on a reception unit included in a measurement unit selected from a plurality of the measurement units connected to the connection unit;
a third obtaining unit configured to obtain fourth information on a light irradiation unit and fifth information on a reception unit related to a measurement unit required in an examination to corresponding to the first information on the examination order;
a determination unit configured to determine whether the light irradiation unit and the reception unit included in the selected measurement unit are suitable for the examination order in accordance with the second information on the light irradiation unit and the third information on the reception unit included in the selected measurement unit and the fourth information on the light irradiation unit and the fifth information on the reception unit related to the measurement unit required in the examination corresponding to the first information on the examination order; and
a setting unit configured to set device parameters of the light irradiation unit and the reception unit included in the selected measurement unit on the basis of the first information related to the examination order in a case that the light irradiation unit and the reception unit included in the selected measurement unit are suitable for the examination order.

2. The apparatus according to claim 1, wherein the one or more processors further function as a notification controller configured to cause a notification unit to perform a notification indicating a result of the determination, performed by the determination unit, as to whether the selected measurement unit is suitable for the examination order.

3. The apparatus according to claim 2, wherein the notification unit is a display unit capable of displaying information on the result of the determination as to whether the selected measurement unit is suitable for the examination order.

4. The apparatus according to claim 2, wherein the measurement unit includes the notification unit.

5. The apparatus according to claim 2, wherein, in a case where it is determined that the selected measurement unit is not suitable for the examination order, the notification controller causes the notification unit to perform a notification indicating one of the measurement units connected to the connection unit which is suitable for the examination order.

6. The apparatus according to claim 1, wherein the one or more processors further functions as:
a third obtaining unit configured to obtain information on a measurement unit required for an examination corresponding to the information on the examination order in accordance with the information on the examination order, wherein the determination unit determines whether the selected measurement unit is suitable for the examination order by determining whether the information on the measurement unit required for the examination corresponds to the information on the selected measurement unit.

7. The apparatus according to claim 1, wherein the connection unit is connectable to the measurement unit in a wired manner or a wireless manner.

8. The apparatus according to claim 1, wherein the one or more processors further functions as a setting unit configured to set an apparatus parameter of the measurement unit in accordance with the information on the examination order in a case where it is determined that the selected measurement unit is suitable for the examination order.

9. The apparatus according to claim 1, wherein the one or more processors further functions as:
- a fourth obtaining unit configured to obtain information on the apparatus parameter of the measurement unit required for the examination corresponding to the information on the examination order in accordance with the information on the examination order; and
- a setting unit configured to set an apparatus parameter of the selected measurement unit in accordance with the information on the apparatus parameter obtained by the fourth obtaining unit in a case where it is determined that the selected measurement unit is suitable for the examination order.

10. The apparatus according to claim 1, wherein the information on the examination order includes at least one of information on an examination target, information on an examination portion, and information on an examination depth.

11. The apparatus according to claim 1, wherein the one or more processors further functions as a setting unit configured to set a wavelength of the light emitted by the light irradiation unit in accordance with the information on the examination order in a case where it is determined that the selected measurement unit is suitable for the examination order.

12. The apparatus according to 1, wherein the first obtaining unit obtains the information on the examination order in accordance with information based on an instruction issued by an operator.

13. The apparatus according to claim 1, wherein the second obtaining unit obtains information on the selected measurement unit in accordance with the information based on the instruction issued by the operator.

14. An examination support method employed in an examination using a plurality of measurement units which each including a light irradiation unit which irradiates a subject with light and a reception unit which receives an acoustic wave generated from the subject which is irradiated with the light, the examination support method comprising:
- obtaining first information on an examination order;
- obtaining second information on a light irradiation unit and third information on a reception unit included in a measurement unit selected from the plurality of measurement units;
- obtaining fourth information on a light irradiation unit and fifth information on a reception unit related to a measurement unit required in an examination corresponding to the first information on the examination order;
- determining whether the light irradiation unit and the reception included in the selected measurement unit are suitable for the examination order in accordance with the second information on the light irradiation unit and the third information on the reception unit included in the selected measurement unit and the fourth information on the light irradiation unit and the fifth information on the reception unit related to the measurement unit required in the examination corresponding to the first information on the examination order; and
- setting device parameters of the light irradiation unit and the reception unit included in the selected measurement on the basis of the first information related to the examination order in a case that the light irradiation unit and the reception unit included in the selected measurement unit are suitable for the examination order.

15. A non-transitory computer-readable storage medium which stores a program which causes a computer to execute the examination support method set forth in claim 14.

* * * * *